United States Patent
Bates et al.

(10) Patent No.: US 6,348,056 B1
(45) Date of Patent: Feb. 19, 2002

(54) MEDICAL RETRIEVAL DEVICE WITH RELEASABLE RETRIEVAL BASKET

(75) Inventors: James S. Bates, Bloomington, IN (US); Srinivas Nishtala, Waltham, MA (US); James A. Teague, Spencer, IN (US); Michael S. H. Chu, Brookline, MA (US)

(73) Assignee: SCImed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/369,226

(22) Filed: Aug. 6, 1999

(51) Int. Cl.⁷ .................................................. A61B 17/32
(52) U.S. Cl. ...................... 606/114; 606/113; 606/110; 604/22
(58) Field of Search ................................ 606/114, 110, 606/127, 113; 604/22

(56) References Cited

U.S. PATENT DOCUMENTS

| | | |
|---|---|---|
| 1,677,671 A | 7/1928 | Councill |
| 2,556,783 A | 6/1951 | Wallace .................... 128/321 |
| 2,943,626 A | 7/1960 | Dormia |
| 3,008,467 A | 11/1961 | Morris ...................... 606/127 |
| 3,108,593 A | 10/1963 | Glassman |
| 3,137,298 A | 6/1964 | Glassman |
| 3,472,230 A | 10/1969 | Fogarty |
| 3,791,387 A | 2/1974 | Itoh |
| 4,046,149 A | * 9/1977 | Komiya .................... 606/127 |
| 4,046,150 A | 9/1977 | Schwartz et al. |
| 4,198,960 A | 4/1980 | Utsugi |
| 4,299,225 A | 11/1981 | Glassman |
| 4,347,846 A | 9/1982 | Dormia |
| 4,557,255 A | 12/1985 | Goodman |
| 4,590,938 A | 5/1986 | Segura et al. |
| 4,611,594 A | 9/1986 | Grayhack et al. |
| 4,612,931 A | 9/1986 | Dormia |
| 4,625,726 A | 12/1986 | Duthoy ....................... 128/328 |
| 4,633,871 A | 1/1987 | Shinozuka |
| 4,655,219 A | 4/1987 | Petruzzi ..................... 128/321 |

(List continued on next page.)

FOREIGN PATENT DOCUMENTS

| | | |
|---|---|---|
| DE | 2804058 | 8/1978 |
| DE | 3633527 A1 | 4/1988 |
| DE | 4025799 A1 | 2/1992 |
| EP | 0 410 561 A1 | 1/1991 |
| FR | 2275187 | 1/1976 |
| JP | 3-205043 | 9/1991 |
| JP | 53-30875 | 12/1993 |
| RU | 2022528 | 11/1994 |
| SU | 1036325 A | 8/1983 |
| WO | 92/05828 | 4/1992 |
| WO | 92/16153 | 10/1992 |
| WO | 95/05129 | 2/1995 |
| WO | 96/01591 | 1/1996 |
| WO | 96/23446 | 8/1996 |
| WO | 99/16363 | 4/1999 |

OTHER PUBLICATIONS

Boston Scientific Corporation, Second Annual Meeting of the Microvasive Endourology Board, Oct. 2–4, 1997, "Releasable Baskets: Clinical Need: Improved Calculi Releasability", with attached Confidential Information Memorandum.

Phan et al., "Ureteric Retrieval Net: Comparison with Stone Extraction by Dormia Baskets in an In Vitro Porcine Model," *Brit. J. Urol.*, 73: 33–36, 1994.

*Primary Examiner*—Gene Mancene
*Assistant Examiner*—Michael B. Priddy
(74) *Attorney, Agent, or Firm*—Testa, Hurwitz and Thibeault, LLP

(57) ABSTRACT

Baskets with multiple portions and multiple deployed configurations allow the capture and release of material within the body.

12 Claims, 15 Drawing Sheets

U.S. PATENT DOCUMENTS

| | | | |
|---|---|---|---|
| 4,741,335 A | 5/1988 | Okada | |
| 4,790,812 A | 12/1988 | Hawkins, Jr. et al. | |
| 4,807,626 A | 2/1989 | McGirr | 128/328 |
| 4,865,017 A * | 9/1989 | Shinozuka | 606/127 |
| 4,927,426 A | 5/1990 | Dretler | |
| 4,997,435 A | 3/1991 | Demeter | |
| 5,030,201 A | 7/1991 | Palestrant | 604/22 |
| 5,057,114 A | 10/1991 | Wittich et al. | |
| 5,059,199 A * | 10/1991 | Okada et al. | 606/127 |
| 5,064,428 A | 11/1991 | Cope et al. | |
| 5,074,867 A | 12/1991 | Wilk | |
| 5,100,423 A * | 3/1992 | Fearnot | 606/159 |
| 5,147,371 A | 9/1992 | Washington et al. | |
| 5,176,688 A | 1/1993 | Narayan et al. | |
| 5,190,542 A | 3/1993 | Nakao et al. | |
| 5,190,557 A | 3/1993 | Borodulin et al. | |
| 5,192,286 A | 3/1993 | Phan et al. | |
| 5,201,740 A | 4/1993 | Nakao et al. | |
| 5,207,686 A * | 5/1993 | Dolgin | 606/113 |
| 5,330,482 A * | 7/1994 | Gibbs et al. | 606/113 |
| 5,376,100 A * | 12/1994 | Lefebvre | 606/180 |
| 5,496,330 A | 3/1996 | Bates et al. | 606/127 |
| 5,549,626 A | 8/1996 | Miller et al. | 606/200 |
| 5,658,296 A | 8/1997 | Bates et al. | 606/127 |
| 5,720,764 A * | 2/1998 | Naderlinger | 606/200 |
| 5,755,790 A | 5/1998 | Chevillon et al. | 606/200 |
| 5,788,710 A * | 8/1998 | Bates et al. | 606/127 |
| 5,792,145 A * | 8/1998 | Bates et al. | 606/127 |
| 5,817,104 A * | 10/1998 | Bilitz et al. | 606/127 |
| 5,836,968 A | 11/1998 | Simon et al. | 606/200 |
| 5,954,742 A * | 9/1999 | Osypka | 606/198 |
| 5,957,932 A * | 9/1999 | Bates et al. | 606/127 |
| 6,077,274 A * | 6/2000 | Ouchi et al. | 606/113 |
| 6,093,196 A * | 7/2000 | Okada | 606/127 |
| 6,099,534 A * | 8/2000 | Bates et al. | 606/127 |
| 6,168,603 B1 | 1/2001 | Leslie et al. | |
| 6,187,017 B1 | 2/2001 | Gregory, Jr. | 606/127 |

\* cited by examiner

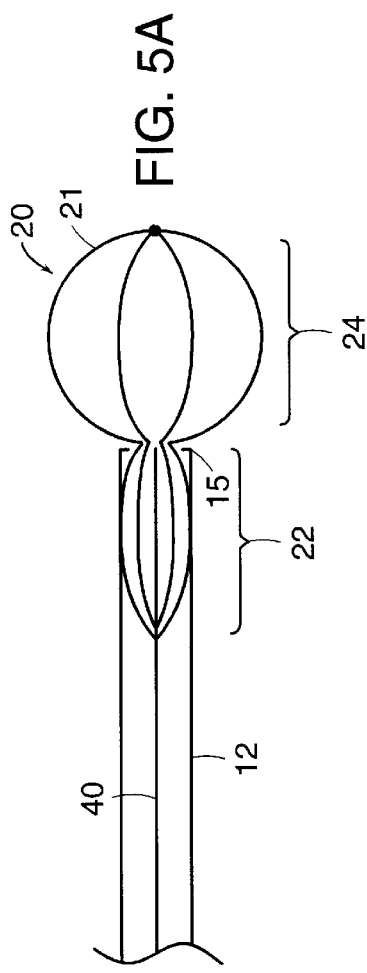
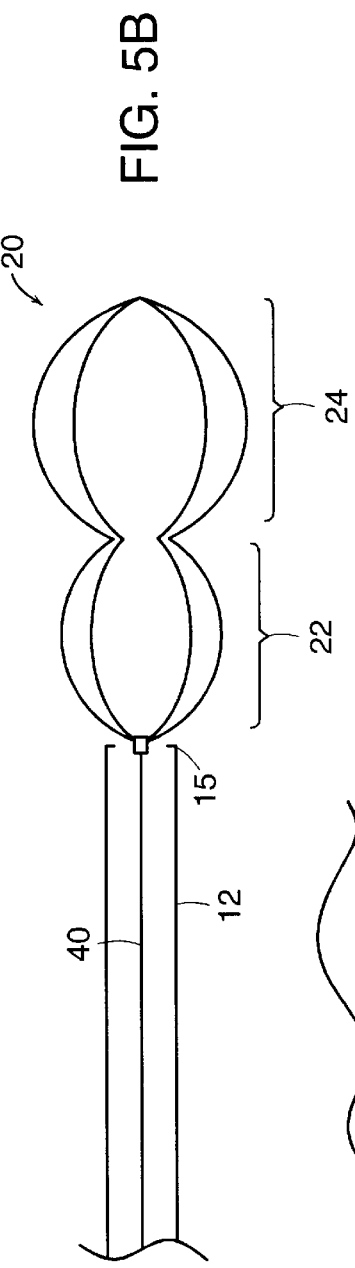
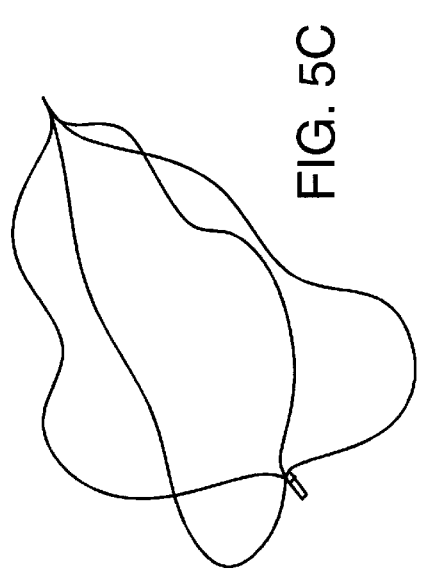

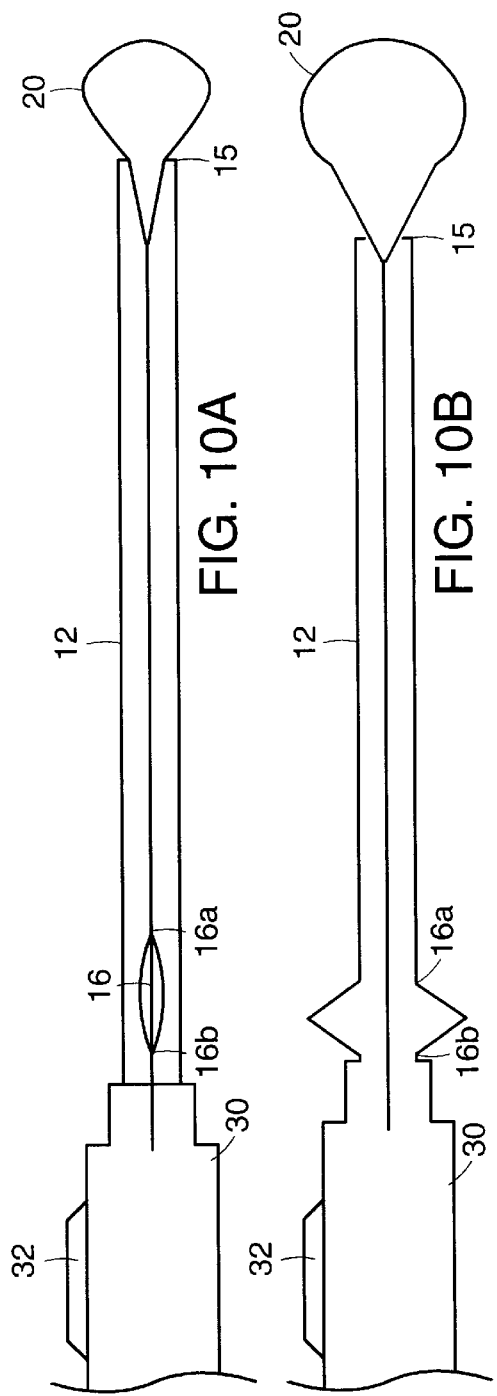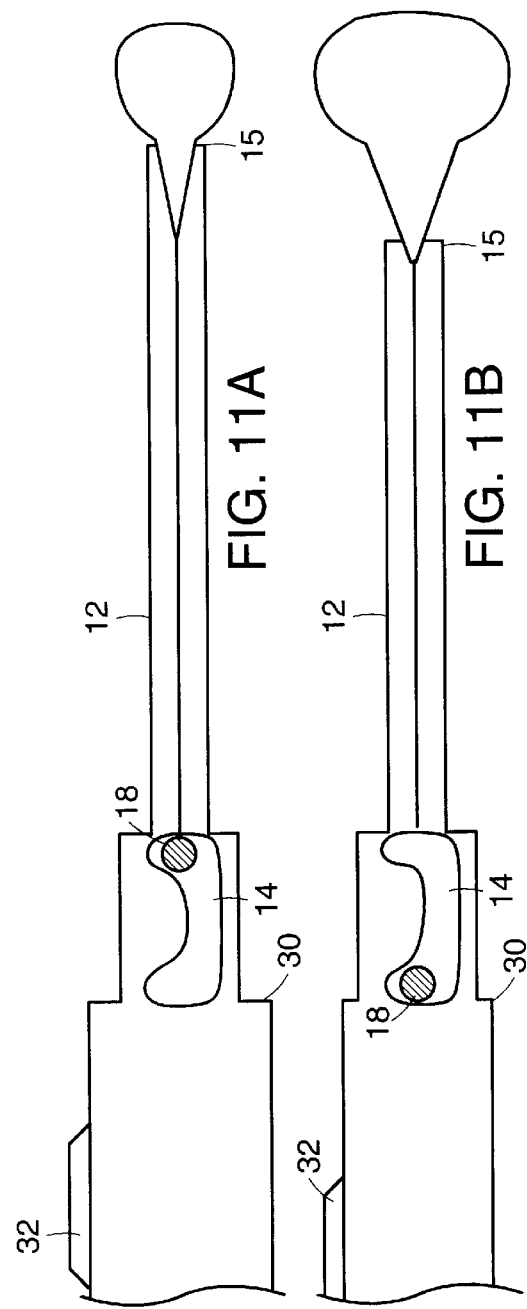

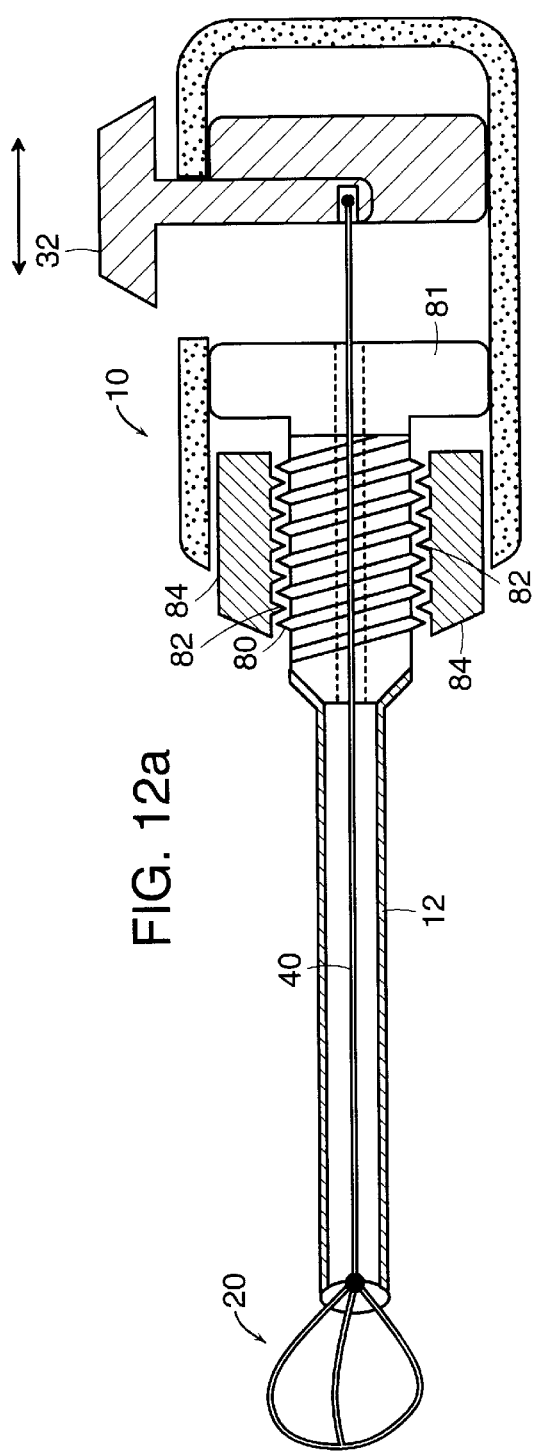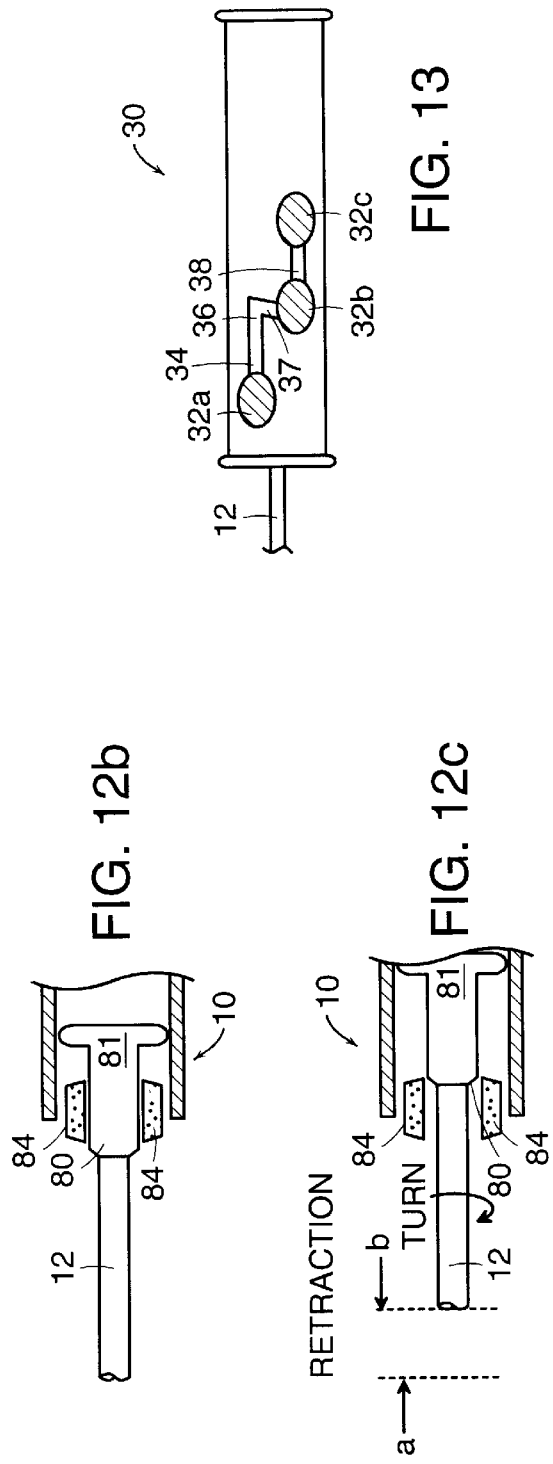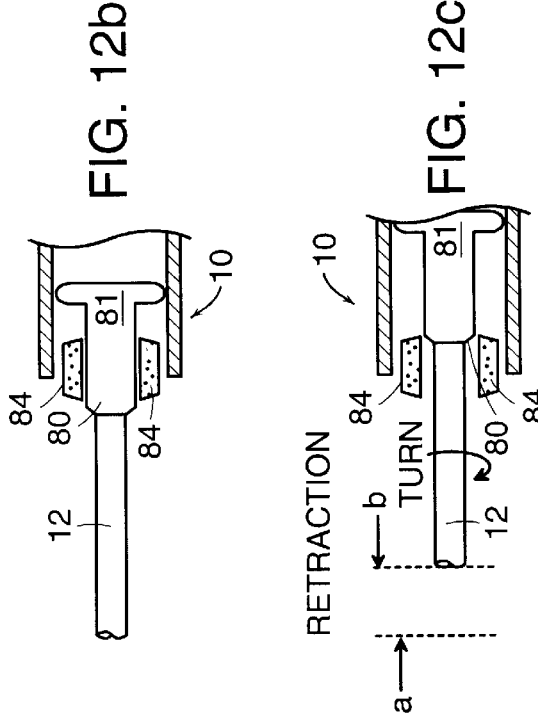

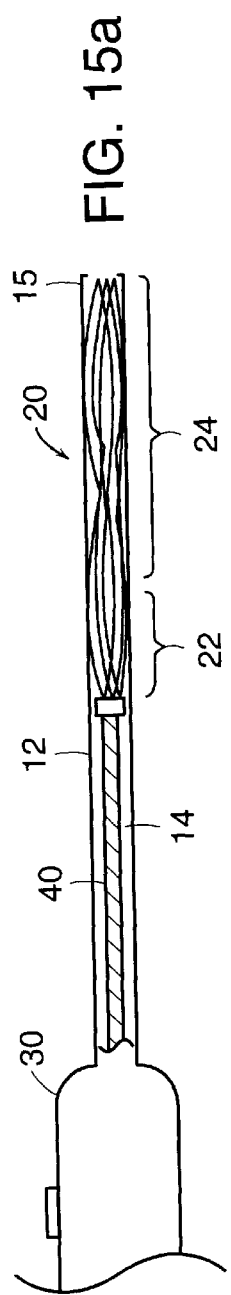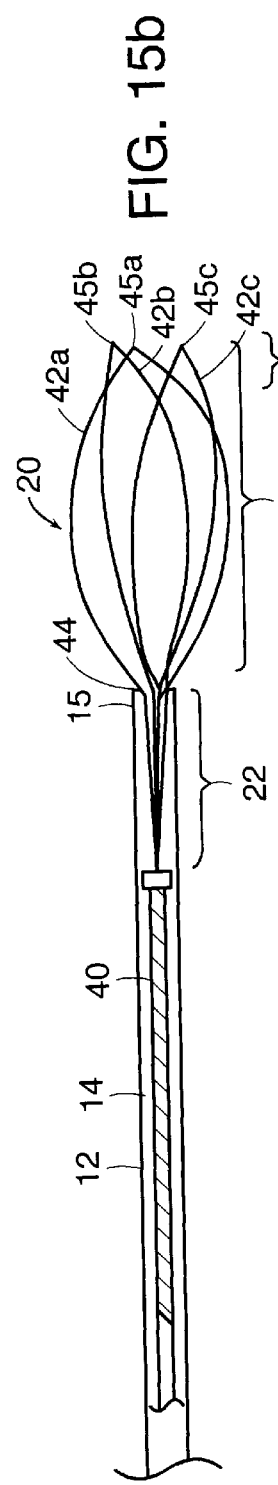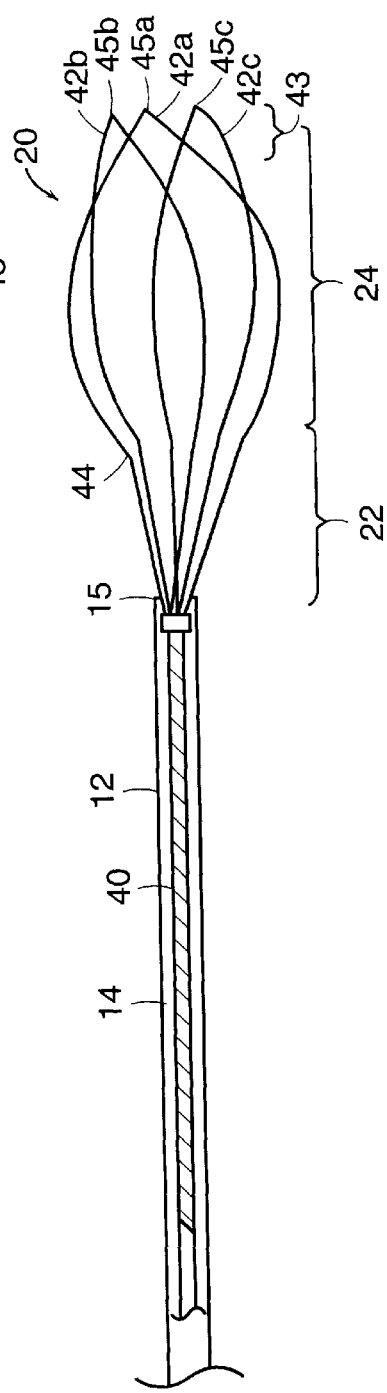

MEDICAL RETRIEVAL DEVICE WITH RELEASABLE RETRIEVAL BASKET

TECHNICAL FIELD

This invention generally relates to medical instruments such as retrieval devices for retrieving material from within a body. More particularly, the invention relates to retrieval devices for capturing and releasing stones such as urinary tract stones, gall stones, and other biological materials.

BACKGROUND INFORMATION

Medical retrieval devices generally are used to retrieve biological and foreign material from the body including stones. Such medical retrieval devices may be used through an endoscope or a laparoscope.

One type of known device has a sheath and a retrieval assembly such as a basket that is movable in and out of the sheath. When the basket is within the sheath, the basket assumes a collapsed, reduced diameter profile. When the sheath is retracted relative to the basket or the basket is moved beyond the end of the sheath, the basket expands to a relatively larger diameter than when the basket is enclosed within the sheath. Generally, the contour of known baskets is round or oval and is formed by a plurality of legs.

With many known retrieval devices, it is technically difficult to release captured material such as a stone from the retrieval assembly once the stone is captured. In some patients, for example, a cicatrix or some other constriction that reduces the diameter of the lumen of the tract may form in the tract in which the stone is lodged because of recurrent trauma caused by the stone to the lining of the tract. The narrowed lumen of the tract may not be so narrow so as to interfere with insertion of a retrieval device while the retrieval device is in a collapsed position. However, after the retrieval device is inserted into the tract, the retrieval assembly expanded, and the stone captured within the device, the diameter of the retrieval assembly containing the stone may exceed the inner diameter of the narrowed lumen of the tract or the inner diameter of the orifice of the tract into which the retrieval device is inserted. If an excessive pulling force is used by the operator in an attempt to remove the retrieval device and stone, the retrieval device may traumatize the orifice or the lining of the tract or, worse, perforate the tract. In addition, the retrieval device may assume an everted configuration causing damage upon being withdrawn from the tract. Under these conditions, the stone must first be released from the retrieval device followed by withdrawal of the collapsed retrieval device from the tract. If the stone can not be released from the retrieval device, more invasive, surgical approaches are required to disengage the stone from the retrieval device and to remove the retrieval device from the body tract.

With most, if not all, current medical retrieval device designs, it is difficult to disengage the stone or other material from the retrieval assembly so that the retrieval device can be collapsed and then removed from the body. Although existing medical instruments are capable of delivering laser energy or chemicals to fragment the stone, these devices are sometimes difficult to position in the body while the retrieval device holding the stone is still in the body.

SUMMARY OF THE INVENTION

It is an object of the invention to provide a medical instrument, i.e., a medical retrieval device with features that permit the device to open to an open position for capturing biological material and to an elongated, expanded open position for releasing captured material. The invention thus involves a device and related method for capturing material in the body such as a stone and then releasing the captured material from the retrieval device while the retrieval device is still positioned in the body. The material can be biological or foreign material such as stones or any of a variety of other types of material within a body. The material can be located in a urinary or biliary tract in the body or elsewhere in the body.

A medical instrument according to the invention is used to treat an internal organ which includes material such as a calculus or a thromboembulus. The medical instrument typically includes a handle, a sheath, and a retrieval assembly such as a basket. An elongated member may extend within the sheath along an axis from a proximal end to a distal end of the sheath. The elongated member and sheath are sized for insertion into a body. The handle is located at the proximal end of the elongated member and the sheath.

The retrieval assembly of the medical retrieval device has at least a proximal portion and a distal portion. The distal portion is used to capture material in a body when the distal portion extends from the distal end of the sheath and while the proximal portion is collapsed within the sheath. The retrieval assembly expands to release captured material when the distal and proximal portions of the retrieval assembly extend from the distal end of the sheath. The contour of each portion of the retrieval assembly may be similar to or different from the other portions of the retrieval assembly.

In one embodiment, the retrieval assembly is a basket. The basket has a plurality of legs, for example, the basket has four legs or the basket has three sets of paired, helical legs. The basket legs can be preformed and the baskets can be atraumatic. Atraumatic baskets have a zero-tip or tipless configuration, and/or may have legs that are D-shaped, B-shaped, V-shaped, or half-round in cross-section such that the legs of the basket are atraumatic.

In an alternate embodiment, the retrieval assembly has a plurality of loops, for example, two opposing loops. The loops of the retrieval assembly are joined at a base of the retrieval assembly. The distal ends of the loops of the retrieval assembly are not joined at the distal end of the retrieval assembly.

In one embodiment of the medical retrieval device of the invention, the proximal portion of the retrieval assembly is generally straight; the contour of the proximal portion being planar rather than curved. Alternatively, at least the proximal portion of the retrieval assembly is bulbous, i.e., the proximal portion is bowed out from the center of the retrieval device when the proximal portion is deployed beyond the distal end of the sheath. Other features of the retrieval assembly can include paired spiral basket legs. The legs of the basket can be, for example, round, oval or half-round. The legs may be preformed.

The invention contemplates any number of portions to the retrieval assembly and is not limited to a proximal and distal portion. For example, the retrieval assembly may have a proximal, intermediate and distal portion.

Other embodiments of this invention include a sheath axially moveable relative to the retrieval assembly. In this embodiment, retraction of the sheath in a direction away from the distal end of the sheath extends the retrieval assembly from the distal end of the sheath. One or more portions of the retrieval assembly are thereby expanded depending on which portions are uncovered by the retracted sheath. Thus, the outer dimensions of the retrieval assembly are adjustable as the retrieval assembly is moved relative to the sheath.

Another embodiment of the invention includes an elongated guide member longitudinally positioned in the lumen of the sheath, operably attached to a proximal end of the retrieval assembly and actuated by at least one actuating member on the handle. Reciprocal axial movement of the elongated guide member moves the retrieval assembly from its enclosed position within the sheath, in and out of the distal end of the sheath and back to its enclosed position within the sheath. As the assembly is moved in and out the sheath, the portions of the retrieval assembly shift between collapsed and opened positions.

In yet another embodiment, the sheath includes a plurality of compressible, generally longitudinal slits for retraction of the sheath. In an alternate embodiment, the sheath includes a plurality of slots, each slot having a slideably movable retractor pin operably attached to the sheath to retract the sheath. In yet another embodiment, retraction of the sheath is accomplished by rotating the sheath on a threaded mechanism. Each of these embodiments of the sheath, i.e., longitudinal slits, slot and pin, and rotatable sheath, allow the operator to make continuous adjustments to the size of the retrieval assembly as it is moved in and out of the sheath.

In yet another aspect, the invention relates to a method for retrieving material from a body. The method comprises inserting a medical retrieval device with a retrieval assembly (such as the instrument described above) into a body, extending the distal portion of the retrieval assembly beyond the end of the sheath, maneuvering the retrieval assembly around the material while the distal portion of the retrieval assembly is extended beyond the distal end of the sheath, capturing the material within the retrieval assembly, withdrawing the proximal and distal portions of the retrieval assembly back into the sheath, and removing the medical instrument and the material captured in the retrieval assembly from the body.

Alternatively, following capture of the material in the distal portion of the retrieval assembly, the proximal portion of the retrieval assembly is extended, the material released from the proximal portion, the proximal and distal portions of the retrieval assembly are withdrawn into the sheath and the medical instrument removed from the body.

In yet another aspect, the invention relates to a method for end-encapsulation or side encapsulation of materials from within a body. The method comprises inserting the medical instrument having a retrieval assembly with loops (such as the device described above) into a body while the loop retrieval assembly is completely enclosed within the sheath. When the material, such as a stone, is approached, the distal portion of the retrieval assembly is extended beyond the distal end of the sheath. If a larger basket is required, the proximal portion of the retrieval assembly may also be extended beyond the distal end of the sheath. While the loops of the distal portion of the retrieval assembly are parted, the retrieval assembly is advanced directly over the stone located at the distal end of the retrieval assembly. The stone is end-encapsulated by advancing the distal end of the retrieval assembly directly over the stone so that the stone enters the retrieval assembly through the opening created by the parted loops of the distal portion of the retrieval assembly. Thus, the loop retrieval assembly can easily "pluck" stones from embedded regions such as the calyces of the kidney. Alternatively, the loop retrieval assembly may capture a stone through or between the loops at the side of the retrieval assembly. The captured material can be released from the loop retrieval assembly by extending the proximal portion of the loop assembly beyond the distal end of the sheath. When the proximal portion as well as the distal portion of the loop assembly is extended beyond the distal end of the sheath, a stone encapsulated within the retrieval assembly can be released from the retrieval assembly or between the parted ends of the loops at the distal end of the retrieval assembly or between or through the loops at the side of the retrieval assembly. If the captured material is not to be released, the sheath is advanced relative to the retrieval assembly causing the assembly loops to grip the captured material. The medical instrument is removed from the body.

BRIEF DESCRIPTION OF THE DRAWINGS

In the drawings, like reference characters generally refer to the same parts throughout the different views. Also the drawings are not necessarily to scale, emphasis instead generally being placed upon illustrating the principles of the invention.

FIG. 5a is an alternate embodiment of the basket according to the invention with the basket in the second basket position.

FIG. 5b is a view of the basket shown in FIG. 5a in the third basket position;

FIG. 5c is a perspective view of the basket shown in FIG. 5b.

FIG. 10a is a plan view of an embodiment of the medical instrument according to the invention having a moveable sheath with a slit.

FIG. 10b is a plan view of an embodiment of the medical instrument according to the invention in FIG. 10a, the sheath retracted from the proximal and distal portions of the retrieval assembly.

FIG. 11a is a plan view of an embodiment of the medical instrument with a sheath having a slot and a pin within the slot according to the invention.

FIG. 11b is the medical instrument illustrated in FIG. 11a with the pin in the proximal position and the proximal and distal portions of the retrieval assembly uncovered by the sheath.

FIG. 12a is a plan view of an embodiment of the medical instrument having a sheath and handle rotatably coupled together by a threaded connection.

FIG. 12b illustrates the embodiment of the invention shown in FIG. 12a with the sheath extended.

FIG. 12c illustrates the embodiment of the invention shown in FIG. 12a with the sheath retracted.

FIG. 13 is a plan view of an embodiment of the medical instrument with a sheath having a "Z" slot according to the invention.

FIG. 15a is a plan view of an embodiment of the medical instrument according to the invention having a retrieval assembly including a plurality of loops.

FIG. 15b is a plan view of the medical instrument illustrated in FIG. 15a with the distal portion of the loop retrieval assembly extended beyond the distal end of the sheath.

FIG. 15c is a plan view of the medical instrument illustrated in FIG. 15a with the proximal and distal portions of the loop retrieval assembly extended beyond the distal end of the sheath.

FIG. 17b is an end-view of the embodiment illustrated in FIG. 17a.

DESCRIPTION

Figure 1:
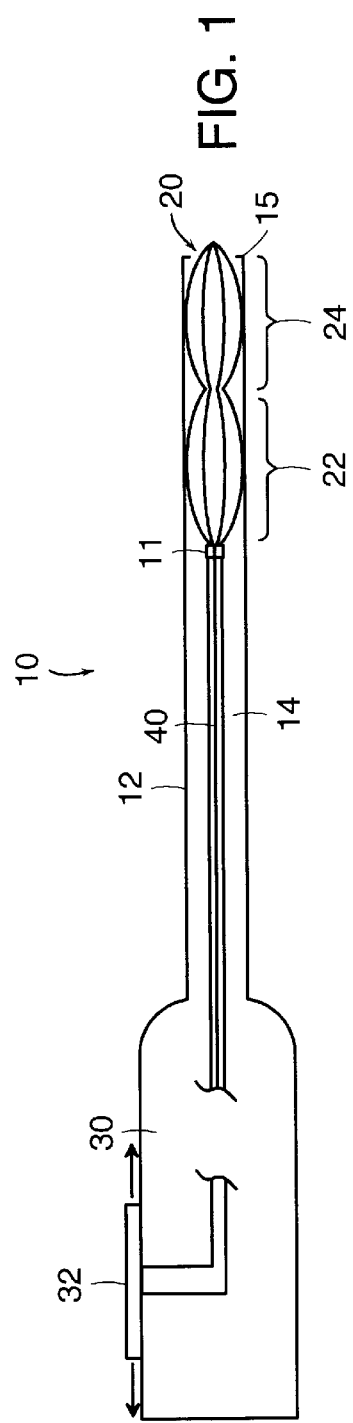
FIG. 1 is a plan view of an embodiment of a medical instrument according to the invention with the proximal and distal portions of the retrieval assembly in a first position.
Figure 2:
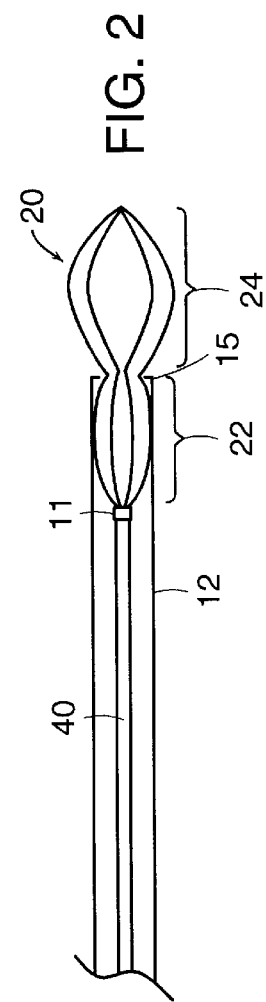
FIG. 2 is a plan view of an embodiment of a medical instrument according to the invention shown in FIG. 1 with the distal portion of the retrieval assembly in a second position.
Figure 3:
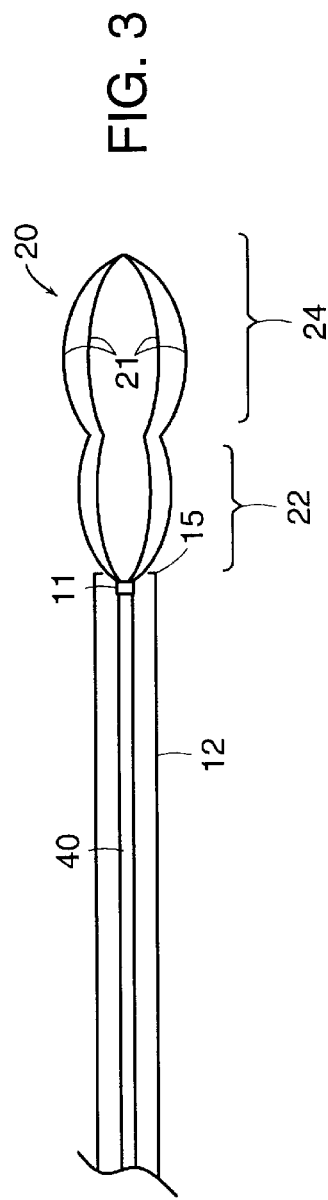
FIG. 3 is a plan view of an embodiment of a medical instrument according to the invention as shown in FIGS. 1 and 2 with the proximal and distal portions of the retrieval assembly in a third position.

Referring to FIGS. 1–3, a medical instrument 10 according to the invention, in general, is shown. The device 10 includes a sheath 12 and a retrieval assembly 20 movable in a lumen 14 of the sheath 12. The outside diameter of the sheath can range from 1.7 Fr. to 8.0 Fr. preferably 3.0 French. The retrieval assembly 20 is the type that can be collapsed within a sheath 12 for entry into the body. A medical instrument 10 or extractor that includes the retrieval assembly 20 of the invention also includes the sheath 12 and a proximal handle 30. The handle 30, sheath 12, and retrieval assembly 20 illustrated in FIGS. 1–3 are not shown in their correct size or proportion to each other. The size of the entire sheath is dimensioned to fit the requirements of the application of the sheath 12 in the body. For example, for urological applications, the size of the device is typically 1.7–8.0 Fr. The sheath 12 has at least one lumen 14 therein, may be made from a single material, and extends from the handle 30 to a distal sheath end 15. An elongated member such as a cable, coil, shaft, guidewire or mandril wire 40 extends within the lumen 14 from at least one actuating mechanism 32 at the device handle 30 to the base 11 of the retrieval assembly 20, where the cable 40 is attached to the retrieval assembly base 11. Operation of one or more actuating mechanisms 32 by an operator causes the retrieval assembly 20 to move in and out of the sheath 12.

Alternatively, the mechanism 32 can cause movement of the sheath 12 to advance the sheath 12 over the stationary retrieval assembly 20 and cable 40 combination, to thereby collapse the retrieval assembly 20 within the sheath 12, and the mechanism 32 can slide the moveable sheath 12 back to expose the stationary retrieval assembly 20 and allow it to open/expand. In general, both types of retrieval assembly/ sheath movement configurations and related handle mechanisms are known, and can be seen in existing product designs available from, for example, Boston Scientific Corporation (Natick, MA). With the retrieval assembly collapsed within the sheath 12 as shown in FIG. 1, the sheath 12 can be inserted into the body by an operator to a site in the body where the material to be retrieved is located (e.g., a stone in the ureter). By placing the retrieval assembly 20 into its open/expanded position, as illustrated in FIGS. 2 and 3, the retrieval assembly 20 dilates the body tract in which it has been placed and can be manipulated by the operator to entrap or capture material within the retrieval assembly 20.

Referring to FIGS. 1–3, in one embodiment, the retrieval assembly is a basket 20 formed by a plurality of legs 21. The legs 21 of the basket or retrieval assembly generally are made from any resilient materials such as stainless steel, nickel titanium (i.e., "Nitinol"), plastic, composite materials, polymers, ceramic-coated metal, or laminations of these materials, for example. The basket is divisible into multiple basket portions such as, for example, a proximal basket portion 22 and a distal basket portion 24. According to the invention, the basket 20 of the device 10 can have more portions than a proximal and distal portion, for example, a proximal basket portion, an intermediate basket portion, a proximal-distal basket portion and a distal basket portion. The proximal end of the proximal basket portion 22 can be operably joined to an elongated member 40 axially disposed within the lumen 14 of the sheath 12.

Figure 4:
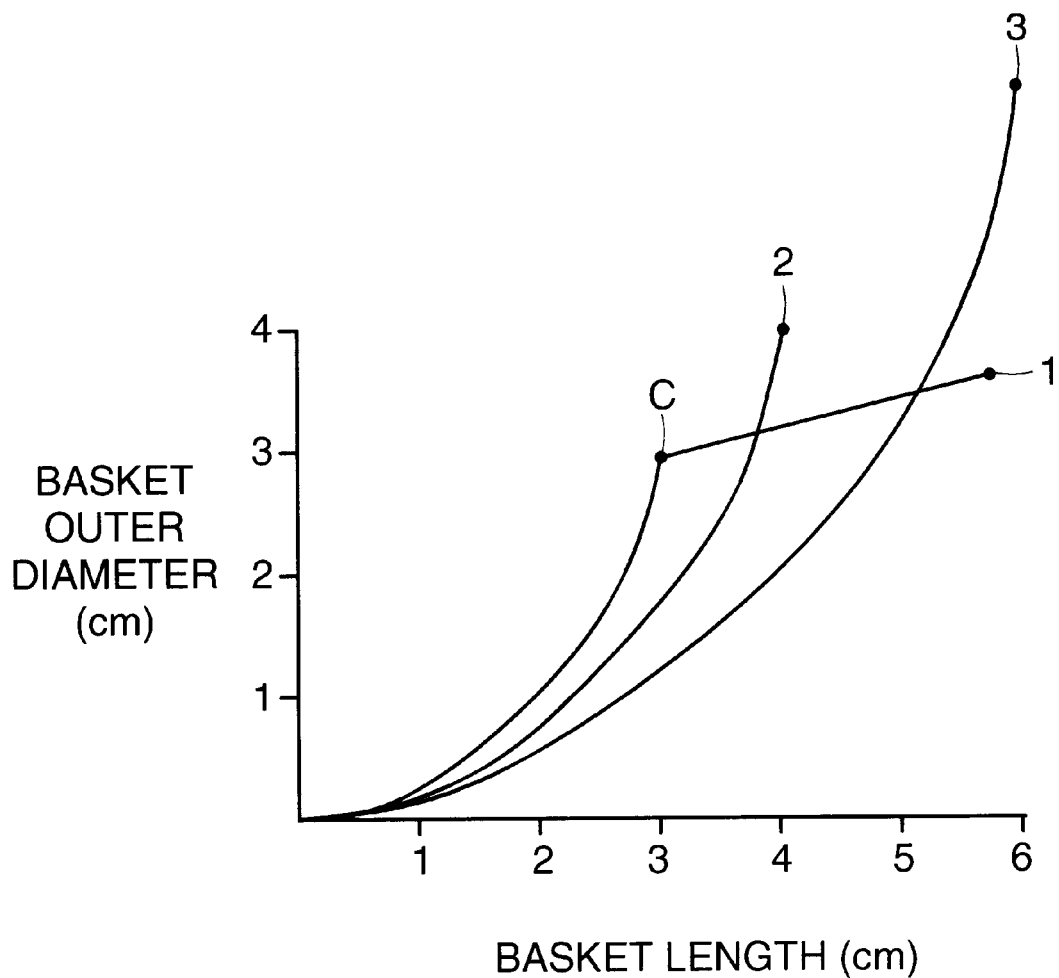
FIG. 4 is a graph showing the relationship between the outer diameter of a retrieval assembly such as a basket with respect to the length of the retrieval assembly that is extended from a distal end of a sheath.

FIG. 4 is a graph showing the relationship between the outer diameter of a retrieval assembly such as a basket relative to the length of the basket as it is extended from the distal end of the sheath. Curve I represents the basket according to the invention and curves 2 and 3 represent conventional baskets. As indicated by curves 2 and 3, expansion of the conventional baskets increases at an exponential rate as the retrieval basket moves from a position in which the retrieval basket is completely enclosed in the sheath to a position in which the basket is completely extended beyond the end of a sheath. In contrast, as indicated by curve 1, the retrieval assembly 20 of the present invention increases in cross-sectional diameter exponentially from the first position when the entire retrieval assembly 20 is collapsed within the sheath 12 (illustrated in FIG. 1) only up to a point C where the sheath 12 and distal portion 24 of the retrieval assembly 20 are in the second position (illustrated in FIG. 2). Continued relative movement of sheath 12 with respect to the retrieval assembly 20, causes a gradual linear increase in the retrieval assembly cross-section until the proximal portion 22 as well as the distal portion 24 of the retrieval assembly 20 is completely extended from the end of the sheath (as illustrated in FIG. 3).

According to the invention, the proximal and distal portions of the retrieval assembly are collapsed within the sheath in a first position. When the distal portion of the retrieval assembly is extended beyond the end of the sheath, the distal portion of the retrieval assembly expands into a second position. When both the proximal and distal portions of the retrieval assembly are extended beyond the distal end of the sheath and expanded, the retrieval assembly is in a third position. Positions 1 through 3 of the retrieval assembly are positions along a continuum from entirely collapsed to entirely expanded retrieval assembly positions.

The contour of the retrieval assembly of the invention may take a variety of shapes. Referring to FIGS. 5a and 5b by example, an alternate embodiment of a retrieval assembly or basket 20 is shown. As shown in FIG. 5a, the basket legs 21 of the distal basket portion 24 are convex, i.e., the legs 21 are bowed out from the basket center axis. In this embodiment, as the basket moves from the first position to the second position, the distal basket portion 24 assumes a bulbous shape. When the basket 20 is extended further from the end 15 of the sheath 12, the proximal basket portion 22 extends from the end of the sheath 12 expanding as the basket 20 is moved from the second position to the third position, illustrated in FIG. 5b. The overall basket contour assumes a peanut shape, as illustrated in FIG. 5c.

The basket legs 21 of the basket 20 shown in FIGS. 1–3, 5a, and 5b may be preformed or bent before the basket 20 is assembled. The legs can be bent in any manner known to one skilled in the art, for example as detailed in U.S. Pat. No. 5,658,296.

Figure 6:
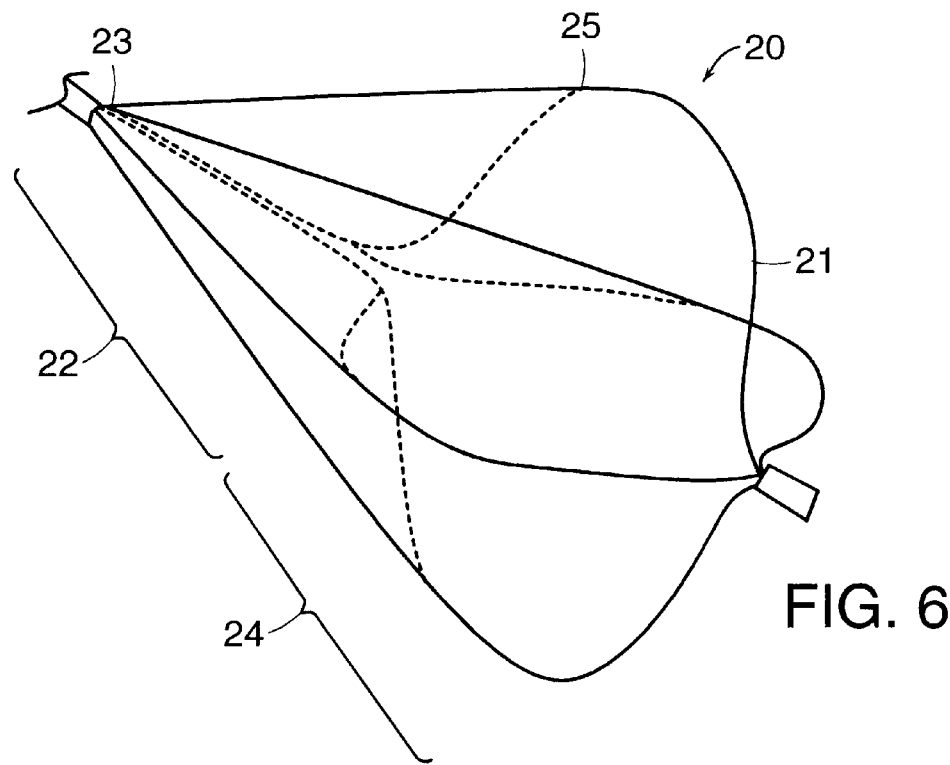
FIG. 6 is a perspective view of an embodiment of the basket according to the invention showing the second and third positions of the basket.

In another embodiment, as shown in FIG. 6, the legs 21 of the proximal portion 22 of the basket 20 are substantially straight. In other words, the proximal end and distal end of a leg 21 of the proximal basket portion 22 are in the same plane. As the basket is extended from the distal end of the sheath (not shown), the distal basket portion 24 expands and the basket assumes a bulbous shape as shown in FIG. 6, second position (inner image). As the basket is extended still further from the distal end of the sheath, the proximal portion 22 of the basket expands. As shown in the third position (outer image) of FIG. 6, the overall contour of the basket 20 in the third position is cone-shaped. The diameter of the proximal basket portion 22 increases uniformly from the proximal end 23 to the distal end 25 of the proximal basket portion 22.

Figure 7A:
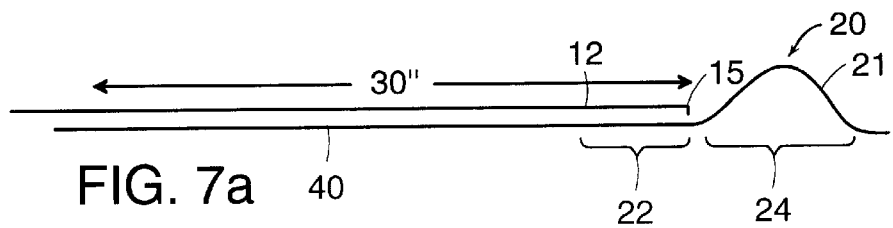
FIG. 7a is a longitudinal section of a portion of the sheath and retrieval assembly of the medical instrument according to the invention having an elongated guide member.
Figure 7B:
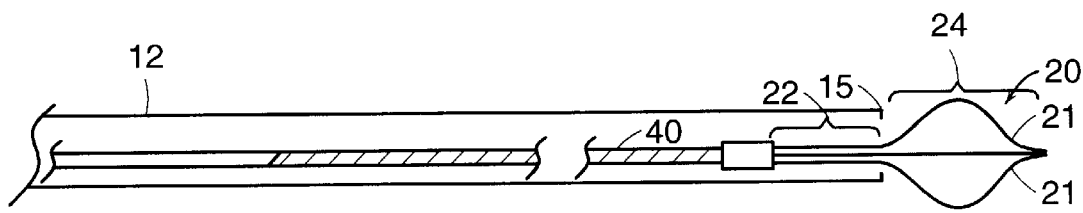
FIG. 7b is a plan view of an embodiment of an elongated guide member operably attached to a retrieval assembly of the medical instrument according to the invention.
Figure 7C:
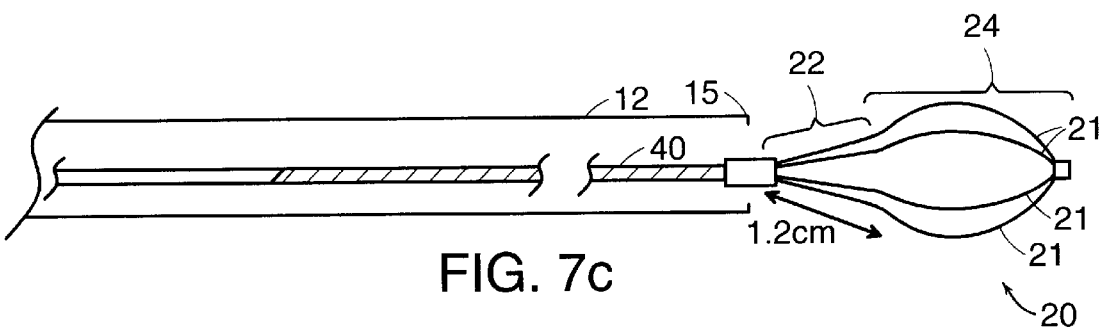
FIG. 7c is a plan view of the fully deployed retrieval assembly shown in FIGS. 7a and 7b.

FIG. 7a shows a schematic of the position of a basket leg 21 relative to the sheath 12 when the basket is in the position illustrated in FIG. 2. As shown in FIG. 7a, the retrieval device such as a basket 20 can be operably joined to the distal end of an elongated guide member 40. The basket 20 comprises a plurality of legs 21 made of a resilient material that allows the basket 20 to expand from the first position, as shown in FIG. 1, to the second position shown in FIGS. 2 and 7a. The resilient material forming the legs can be nickel titanium (Nitinol), stainless steel, or generally any other material or combination of materials that provides strength yet is resilient. In the embodiments of FIGS. 7a–7c, each of the legs 21 have a straight portion in the proximal basket portion 22 and are connected at the proximal end of the leg to the distal end of the elongated member 40. The remaining portion of each of the legs 21 is in the distal basket portion 24 and is bent to form an enlarged basket cross section in the distal basket portion 24. As shown in FIG. 7c, the length of the proximal basket portion 22 can be about 0.394 inches to 0.788 inches. As shown in FIG. 7a, the distance from the proximal end of the elongated guide member 40 to the initial bend in each of the legs of the basket 20 is about 30 inches. The basket 20 is fully deployed when proximal basket portion 22 and distal basket portion 24 are completely extended from the distal end 15 of sheath 12 as illustrated in FIG. 7c.

Figure 8A:
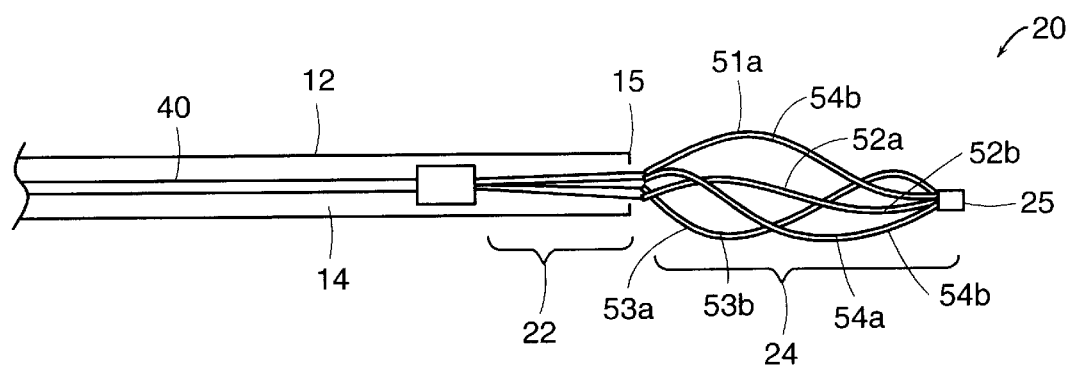
FIG. 8a is a plan view of an embodiment of a retrieval assembly or basket according to the invention having a distal basket portion with spiral legs with the sheath retracted from the distal portion of the basket.
Figure 8B:
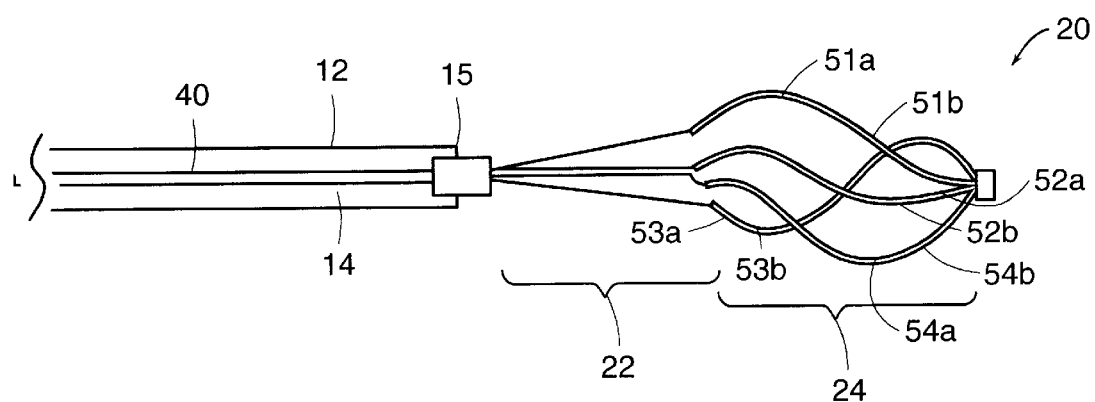
FIG. 8b is the basket of FIG. 8a with the proximal and distal basket portions extended beyond the distal end of the sheath according to the invention.

Referring to FIG. 8a, the distal portion 24 of the basket can be comprised of a plurality of spiral-shaped strands or legs 51–54. The spiral-shaped legs may be paired. As the distal basket portion 24 is extended beyond the end of the sheath 12, the distal basket portion 24 expands into a substantially helical shape as illustrated in FIG. 8a. The basket 20 elongates and expands as the proximal basket portion 22 is extended from the end 15 of the sheath 12 and the basket 20 assumes the third basket position illustrated in FIG. 8b.

The legs of the helical-shaped portion of the basket are constructed similar to the helical leg arrangement disclosed in U.S. Pat. No. 5,496,330. These legs may have a round cross-section and the legs are close to one another. During manufacture of the specific embodiment of FIG. 8a, eight individual wires 51a through 54b are collected together. The distal ends of the wires are soldered or swaged into the cap 25. The wires are separated into pairs corresponding to the strands 51 through 54. Each pair is then formed onto a four-part helix former. Although the wires in a strand, such as wires 51a and 51b associated with strand 51, are formed as a pair of a single strand or thread, the wires are not twisted. Consequently, each of the strands 51 through 54 will be equiangularly spaced, by approximately 90°, but individual wires, such as wires 51a and 51b of a strand, such as strand 51, will be closely angularly spaced. A typical close angular spacing will produce a separation of the wires in a set, such as wires 51a and 51b, by a distance in the range from 0 to 0.5 mm or so.

The increase in the number of wires does not reduce the openings between adjacent strands appreciably, so the effort for moving the basket 20 over calculi is about the same as required to position a prior art four-strand basket. The manufacturing process also prestressed the individual wires 51a through 54b into the helical form shown in FIG. 8a.

The use of multiple wires for a given strand, such as wires 51a and 51b in strand 51, increases the number of contact points with any entrapped calculi. In FIG. 8a, for example, eight wires will contact the calculi rather than four. Moreover, the close equiangular spacing of adjacent wires in a given strand also permits the wires collectively to accommodate any surface unevenness of such calculi surfaces to further increase the reliability with which the basket 20 entraps calculi.

Further, the increase in the number of wires, such as doubling the wires from four to eight in FIG. 8a, occurs without increasing the overall size of the sheath 12 or reducing the strength of the retrieval basket 20. For example, it is possible to replace four individual wires having a diameter of 0.008" in a sheath 12 with an outside diameter of 3.0 Fr with eight wires having a diameter of 0.006" due to the change in packing efficiency without a concomitant reduction in the diameter. Thus, for a given material, the collective strength of the retrieval basket 20 and of the strands 51 through 54 can increase by as much as 50% over a single filament strand of the prior art.

Figure 9:
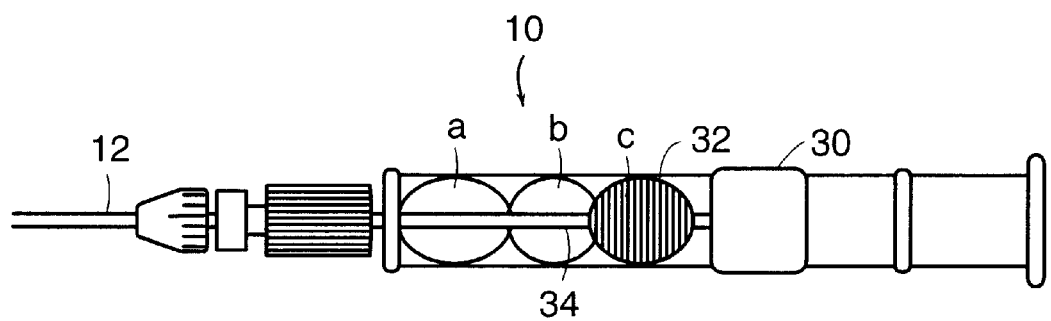
FIG. 9 is a plan view of an embodiment of a handle with a slide adjustment according to the invention.

Referring to FIG. 9, the device 10 also includes a handle 30 at the proximal end of the device. In one embodiment, the handle 30 includes at least one slide actuator 32 operably attached to the sheath 12. The body of the handle 30 is coupled to the basket 20 (not shown) via the elongated member 40 (not shown). The slide adjustment 32 is movable in a groove 34 formed in the handle 30. When the slide adjustment is in position (a), the basket is entirely enclosed within the sheath (FIG. 1). When the slide adjustment 32 is moved to position (b), the distal basket portion 24 is positioned beyond the end 15 of the sheath 12 in the open position shown in FIG. 2. When the slide adjustment 32 is moved to its most proximal position (c), the proximal basket portion along with the distal basket portion is positioned out of the sheath 12 in the position shown in FIG. 3. Further details about the construction of the handle 30 are disclosed in U.S. Pat. No. 5,496,330 incorporated herein by reference.

When the device 10 is stuck in the lumen of a body tract during removal of both the basket 20 and a stone in the basket 20, the operator withdraws the sheath 12 proximally (or advances the basket 20 distally) as shown in FIG. 3 and extends the proximal basket portion 22 beyond the distal end 15 of the sheath 12 to greatly enlarge the basket 20 along the longitudinal and transverse axes of the basket. The gap or distance between basket legs 21 is thereby increased and the basket legs 21 are more maneuverable largely because the distance between the fixed points of the basket legs 21 at the proximal and distal basket ends is increased. The widened gap between basket legs 21 and the enhanced maneuverability of the basket legs 21 allows for easier stone removal via basket manipulation. This feature could also be used to enable easier stone capture.

Withdrawal of the sheath 12 to place the retrieval device or basket 20 in the position shown in FIG. 3 can be accomplished in a number of different ways. The following sheath embodiments allow the operator to select any retrieval assembly size between position 1 (completely enclosed within the sheath) to position 3 (proximal and distal portions extended and completely expanded beyond the distal end of the sheath). In one embodiment, the handle 30 is removable from one or both of the sheath 12 and the elongated member 40. By removing the handle 30 the operator can manually retract the sheath 12 from the proximal basket portion 22 (not shown). By unsheathing the proximal basket portion 22, natural expansion of the resilient legs 21 of the proximal basket portion 22 is accomplished. As described above, the gap between legs 21 is widened and the basket legs 21 become more maneuverable.

Alternatively, in devices with an operable elongated guide member 40, the operator, by removing the handle 30, can manually advance the elongated guide member 40 distally. The proximal basket portion 22, operably attached to the elongated guide member 40, is extended through the distal end 15 of the sheath 12. As in the above-described embodiments, the proximal basket portion 22 expands thereby improving the ease by which stones may be released from the basket 20.

In another embodiment, shown in FIGS. 10a and 10b, a sheath 12 includes a plurality of axially oriented slits 16, such as four slits, spaced around the circumference of the sheath 12. The distal sheath 15 may be manually axially moved in a proximal direction. As the sheath is moved manually, the distal end 16a of the one or more slits 16 is compressed against the proximal end 16b of each respective slit 16. The distal sheath is withdrawn from the proximal portion 22 of the retrieval device thereby extending the proximal portion 22 beyond the end of the sheath 15. The resilient legs 21 of the proximal portion 22 expand as shown in FIG. 10b.

As described in the embodiments above, the gap between the basket legs is widened and the maneuverability of the basket legs is increased. The ease by which a stone may be released by the basket is thereby enhanced.

Alternatively, as illustrated in FIGS. 11a and 11b, a sheath 12 adjacent the handle includes a slot 14. The sheath 12 is operably attached to a pin 18 movable in a slot 14. When the pin 18 moves in the slot 14 from the distal position shown in FIG. 11a to the proximal position shown in FIG. 11b, the sheath 12 also moves in the proximal direction as shown in FIG. 11b. As the sheath 12 moves proximally, the proximal portion 22 of the retrieval assembly expands as it is uncovered by the distal sheath end 15.

In still another embodiment (FIG. 12a), the sheath 12 and the handle 10 are rotatably coupled together by a male threaded connection 80 located at the proximal end of the sheath on the connector 81. The male threaded connection 80 located at the connector 81 located on the proximal end of the sheath 12 engages the female threads 82 positioned on the release knob 84. The relative axial position of the sheath 12 may be altered as illustrated in FIG. 12b by advancing the sheath 12 proximally by rotating the threaded connection 80 relative to the female threads 82 of the release knob 84. The distal end of the sheath is thereby moved proximally from point (a) to point (b) as shown in FIG. 12c and the proximal portion of the retrieval assembly 20 is unsheathed. By rotating the threaded connection 80 relative to the female threads 82 of release knob 84 in the opposite direction, the distal sheath 12 is advanced distally, i.e., from point (b) to point (a) to cover the retrieval assembly 20.

In yet another embodiment, referring to FIG. 13, a handle 30 includes a groove 34 having two separate portions 36 and 38 and a slide adjustment 32 slideably moveable within the groove. The slide adjustment is operably attached to the proximal sheath. When the slide adjustment 32 shown in FIG. 13 moves from the distal end, position (a), of first groove portion 36 to groove portion 37, position (b), the sheath 12 moves between the first and second positions shown in FIGS. 1 and 2, respectively, thereby deploying the distal portion 24 of the retrieval assembly (illustrated in FIG. 2). When the slide adjustment 32 shown in FIG. 13 moves in the second groove portion 38 to the distal end of groove portion 38, position (c), the sheath moves between the second and third positions shown in FIGS. 2 and 3, respectively, exposing the proximal portion 22 of the retrieval assembly. As shown in FIG. 13, the groove 34 including the portions 36, 37 and 38 is generally Z-shaped. Thus, the retrieval assembly moves from the first position of the retrieval assembly shown in FIG. 1 to the second basket position shown in FIG. 2 as slide adjustment 32 is moved proximally in groove portion 36. As the slide adjustment is moved still further proximally into groove portion 38, the proximal portion 22 is extended beyond the end of the sheath 12. Thus, the retrieval assembly 20 moves from the second position to the third position shown in FIG. 3.

The following is a discussion of the operation of the device 10 as described above during retrieval of stones in the body.

Figure 14A:
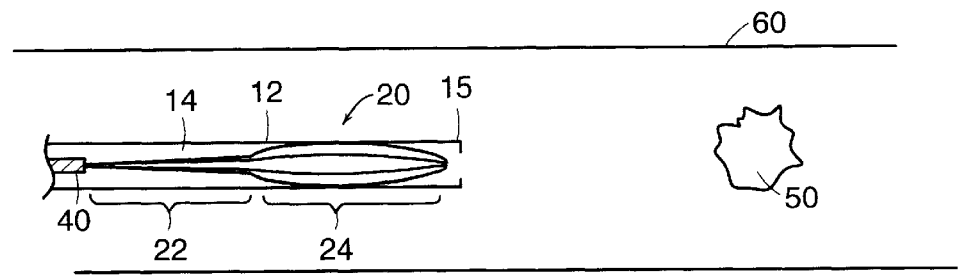
FIG. 14a is a plan view of an embodiment of the medical instrument approaching a stone in the lumen of a body tract with the entire retrieval assembly enclosed within a sheath according to the invention.
Figure 14B:
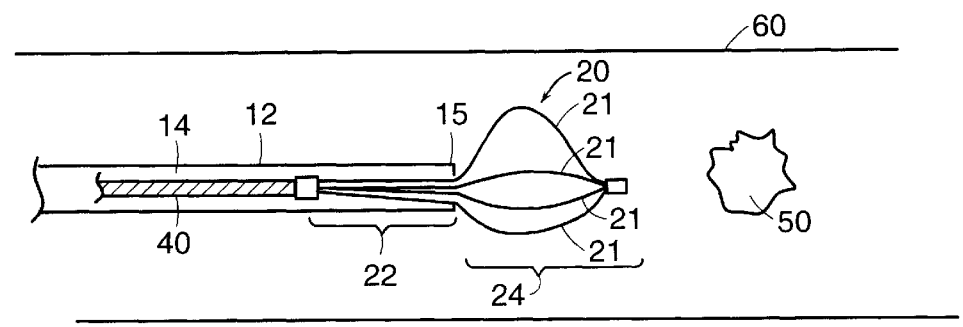
FIG. 14b is a plan view of the medical instrument in FIG. 14a approaching a stone in the lumen of a body tract with the distal portion of the retrieval assembly extended beyond the distal end of the sheath.
Figure 14C:
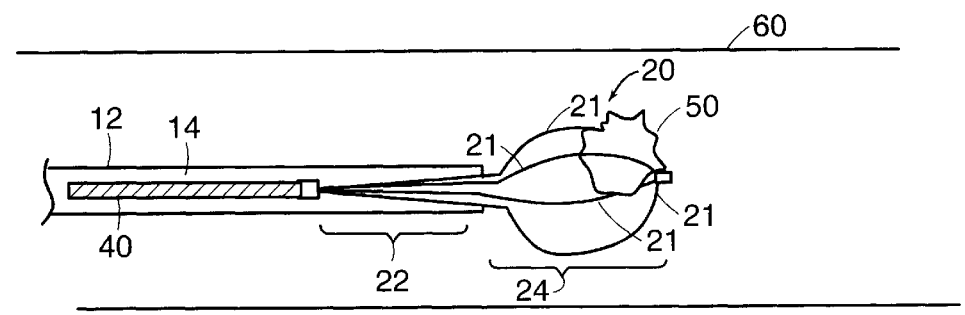
FIG. 14c is a plan view of a stone entering the distal portion of the retrieval assembly through the gaps between the basket legs.

The device according to the invention can be used in a clinical application to retrieve biological or foreign material from within a body. For example, the device in FIGS. 1–3, 5a–5c, 6, 8a and 8b can be used to retrieve a stone (e.g., a stone in the gall bladder, biliary tree, ureter, kidney, urinary bladder, urethra, etc.). The device could also be used to capture a thrombus or embolus within a vessel such as the coronary vessels of the heart or within the pulmonary vasculature. Referring to FIGS. 14a–14d, regardless of the material being retrieved, the device 10 with the retrieval assembly 20 enclosed within a sheath 12 is inserted into a body tract 60. As the distal end of the sheath approaches a stone 50, as illustrated in FIG. 14a, or passes to one side of a stone 50, the distal portion 24 of the retrieval assembly is moved relative to the sheath 12 and extended beyond the distal end 15 of sheath 12. Thus, the retrieval assembly 20 is moved from the first position to a second position as shown in FIG. 14b. The retrieval assembly 20 is maneuvered around the stone 50 to capture the stone 50 within the retrieval assembly 20 after the stone 50 moves through the gap between the legs 21 of the retrieval assembly 20, illustrated in FIG. 14c. The stone 50 may be approached from the side or from the proximal or distal end of the retrieval assembly. The stone 50 is captured in the retrieval assembly 20. The stone 50 can now be removed from the body tract by withdrawing the entire medical instrument 10 with the retrieval assembly 20 containing the stone 50, from the body tract 60.

Figure 14D:
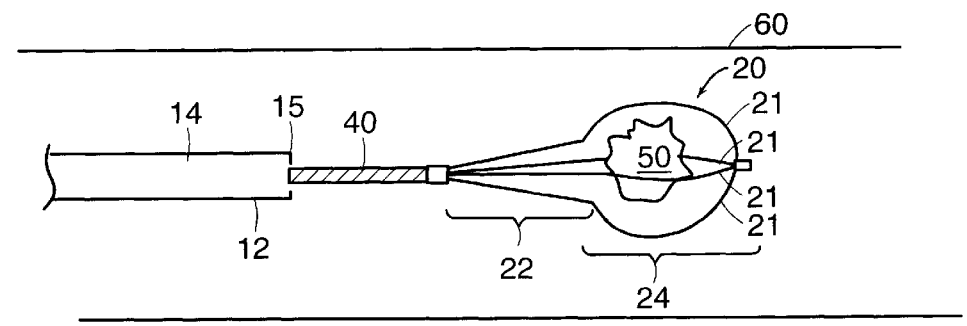
FIG. 14d is a plan view of a stone captured within the distal basket portion of the retrieval assembly with the distal portion and the proximal portion extended from the distal end of the sheath.

In some clinical situations, however, it may be desirable to release the stone or other captured material from the retrieval assembly before removing the medical instrument from the body. For example, the retrieval assembly can be used to relocate stones within the body to a more accessible location for lithotripsy or other forms of stone treatment. As illustrated in FIG. 14d, this can be done by extending the distal portion 24 and proximal portion 22 of the retrieval assembly 20, such as a basket, from the end 15 of the sheath 12. Thus, the basket 20 is moved from the second position to the third position. The distance between the basket legs 21 is increased enhancing the ease by which the stone 50 can be released from the basket 20 between the basket legs 21. After the stone 50 is released from the basket 20, basket 20 is moved from the third position through the second to the first position wherein the basket is entirely enclosed within the sheath 12, as illustrated in FIG. 14a. The retrieval device can now be removed from the body or manipulated in another position in the body to capture a stone or other material.

Referring to FIGS. 15a–15c, in another aspect of the invention, the medical instrument is useful for end-encapsulation or side-encapsulation of material within a body. In one embodiment of this aspect of the invention, the distal portion 24 of the retrieval assembly 20 includes three or more wire loops 42. Each of the retrieval assembly loops 42 has an apex 45. The apex 45 of each retrieval assembly loop 42 is positioned at the distal end of the retrieval assembly 20 and is unattached to the other loops 42 at the distal end 43 of the loops. The contour of the retrieval assembly loops 42 in the distal portion 24 of the retrieval assembly 20 is generally oval but may be round, oblong or asymmetrical.

Each of the proximal ends 44 of the distal portion 24 of the loops of the retrieval assembly are continuous with the proximal retrieval assembly portion 22. The proximal portion 22 of the retrieval assembly 20 can be operably attached to the distal end of elongated member 40. The portion of the retrieval assembly loops 42 corresponding to the proximal portion 22 are generally straight, best illustrated in FIGS. 15b and 15c.

The loop retrieval assembly 20 is moveable between at least a first position, a second position, and a third position as described above. Referring to FIG. 15a, when the loop retrieval assembly 20 is entirely enclosed by and collapsed within the sheath 12, the retrieval assembly 20 is in the first position. When the loop retrieval assembly 20 is moved relative to the sheath 12 by advancing the elongated member 40 distally, retracting the sheath 12, or a combination of both, the distal portion 24 of the loop retrieval assembly 20 is extended beyond the end 15 of the sheath 12 and the loop retrieval assembly 20 assumes the second position as illustrated in FIG. 15b. As the loop retrieval assembly 20 is further advanced from the end 15 of the sheath 12, the proximal retrieval assembly portion 22 along with the distal retrieval assembly portion 24 is unsheathed and the loop retrieval assembly 20 assumes an elongated expanded shape in the third retrieval assembly position as illustrated in FIG. 15c.

Figure 15F:
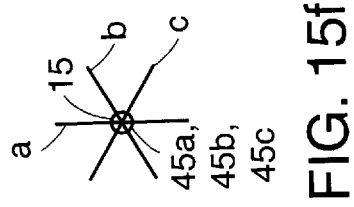
FIG. 15f is an end-view of one embodiment of the loop configuration of the loop retrieval assembly in FIG. 15d.
Figure 15E:
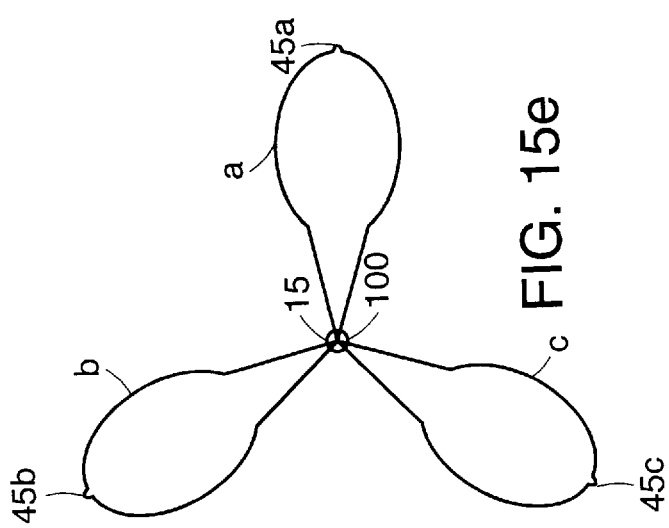
FIG. 15e is an end-view of the loop retrieval assembly illustrated in FIG. 15c with the retrieval assembly fully deployed.

Each of the retrieval assembly loops 42 have an unattached or free end 43 at the distal end of the distal retrieval assembly portion 24. Referring to FIG. 15*b*, when the retrieval assembly 20 is in the second (open) position or third (expanded, elongated position), the unattached ends 43 of the retrieval assembly loops 42 are parted. When the retrieval assembly 20 is in the first (collapsed) position, as shown in FIG. 15*a*, the unattached ends 43 of the loops 42 are juxtaposed in that they are positioned closely together. The retrieval assembly 20 may assume any position between the expanded, elongated and closed positions. For example, the unattached ends 43 of the retrieval assembly loops 42 may be parted to any intermediate position along an arc drawn by the unattached ends 43 of the retrieval assembly loops 42 as the loops 42 move between the first (closed) position illustrated in FIG. 15*a* and the third (expanded and elongated) position illustrated in FIG. 15*c*. An end-on view of the retrieval assembly in the third position illustrated in FIG. 15*c* is shown in FIG. 15*e*.

Figure 15H:
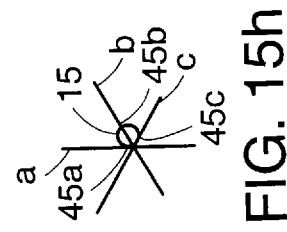
FIG. 15h is an end-view of one embodiment of the loop configuration of the loop retrieval assembly in FIG. 15d.
Figure 15D:
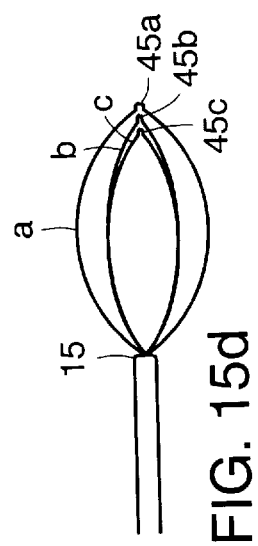
FIG. 15d is a side-view of the loop retrieval assembly in position 2 having loops of different lengths.
Figure 15G:
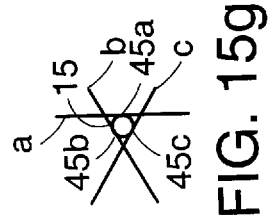
FIG. 15g is an end-view of one embodiment of the loop configuration of the loop retrieval assembly in FIG. 15d.

The length of each of the loops 42 can be the same, or one can be slightly longer than the other such that the ends 45 do not exactly align upon closure. Having one loop 42 longer than the other has been shown to help in collapsing the retrieval assembly 20 to its smallest profile such that it more easily fits into a sheath 12. A side view of a retrieval assembly having loops of different lengths in the second position is shown in FIG. 15*d*. Loops 42*a*, 42*b*, and 42*c* have different lengths. The ends 45*a*, 45*b*, and 45*c* of the loops in position 2 may be aligned axially as shown in FIG. 15*f*, radially around the opening of the end 15 of sheath 12 as shown in FIG. 15*g*, or may be eccentrically positioned around the opening of the end 15 of the sheath 12 as shown in FIG. 15*h* when the loop retrieval assembly is in position 2.

Figure 15I:
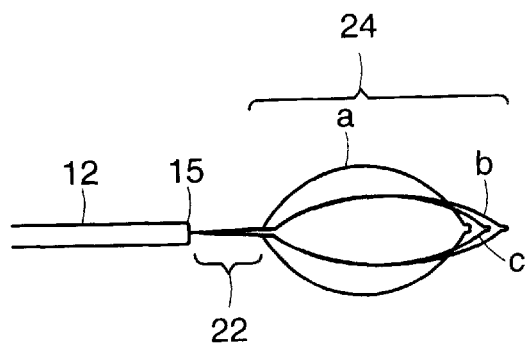
FIG. 15i is a side-view of an embodiment of the loop retrieval assembly in position 3 having loops of different lengths.
Figure 15L:
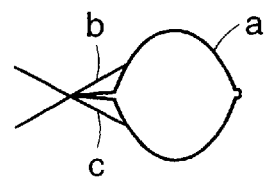
FIG. 15l is an end-view of the loop retrieval assembly illustrated in FIG. 15i.
Figure 15J:
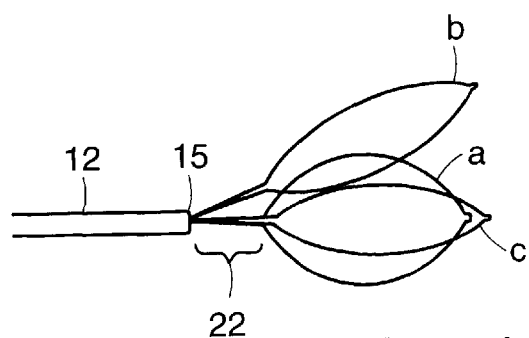
FIG. 15j is a side-view of an embodiment of the loop retrieval assembly in position 3 having loops of different lengths.
Figure 15M:
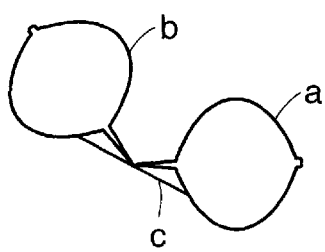
FIG. 15m is an end-view of the loop retrieval assembly illustrated in FIG. 15j.
Figure 15K:
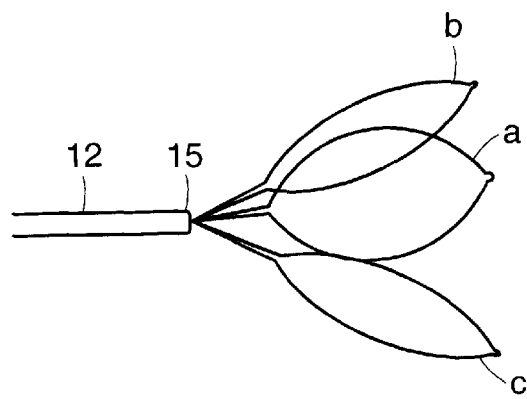
FIG. 15k is a side-view of an embodiment of the loop retrieval assembly in position 3 having loops of different lengths.
Figure 15N:
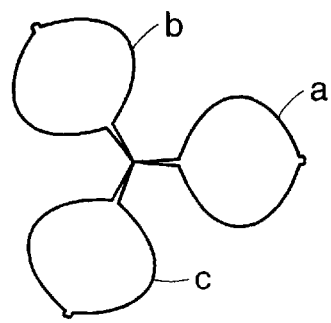
FIG. 15n is an end-view of the loop retrieval assembly illustrated in FIG. 15k.

In position 3, the loops of the retrieval assembly may be oriented as shown by side view in FIG. 15*i*, 15*j*, or 15*k*, or end-view in FIG. 15*l*, 15*m*, or 15*n*, respectively.

In the disclosed embodiment, the retrieval assembly loops 42 are made from a metal material. For example, retrieval assembly loop material can be specialty metals such as 455 custom stainless steel or NiTi ("Nitinol"). Alternatively, the retrieval assembly loops can be made from plastic, composite materials, polymers, ceramic-coated metals or laminations of these materials, or other material. Also, the retrieval assembly loops may be formed from laminations of the above materials. In one embodiment, the retrieval assembly loops are made of flat wire (i.e., wire that is rectangular in cross section) but may be round, D-shape, or other cross-sectional shape.

Figure 16A:
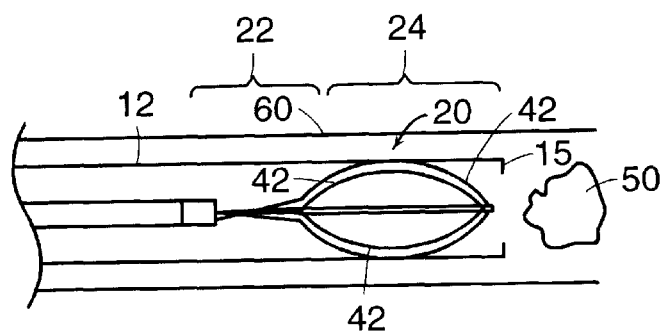
FIG. 16a is a plan view of an embodiment of the medical instrument according to the invention having a loop retrieval assembly enclosed within a sheath approaching a stone in a body tract.
Figure 16B:
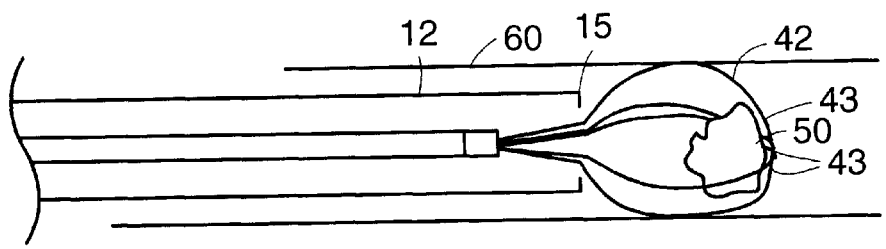
FIG. 16b is a plan view of the medical instrument illustrated in FIG. 16a with the distal portion of the retrieval assembly extended beyond the distal end of the sheath in the second position.
Figure 16C:
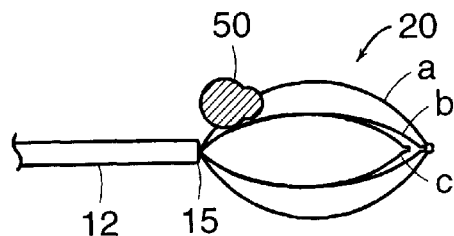
FIG. 16c is a side-view of a loop retrieval assembly capturing a stone through the gaps between the loops.
Figure 16D:
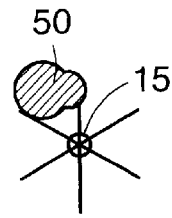
FIG. 16d is an end-view of a loop retrieval assembly capturing a stone through the gaps between the loops.
Figure 16F:
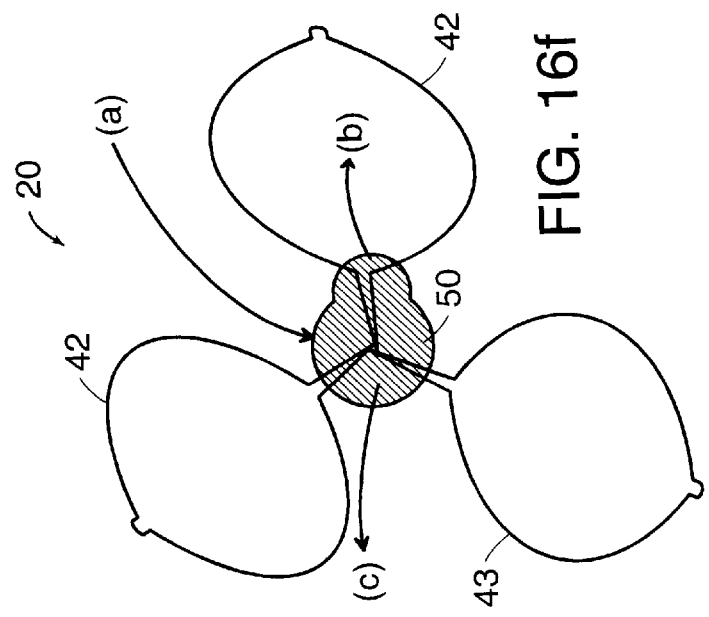
FIG. 16f is an end-view of a loop retrieval assembly in the third position with a stone.
Figure 16E:
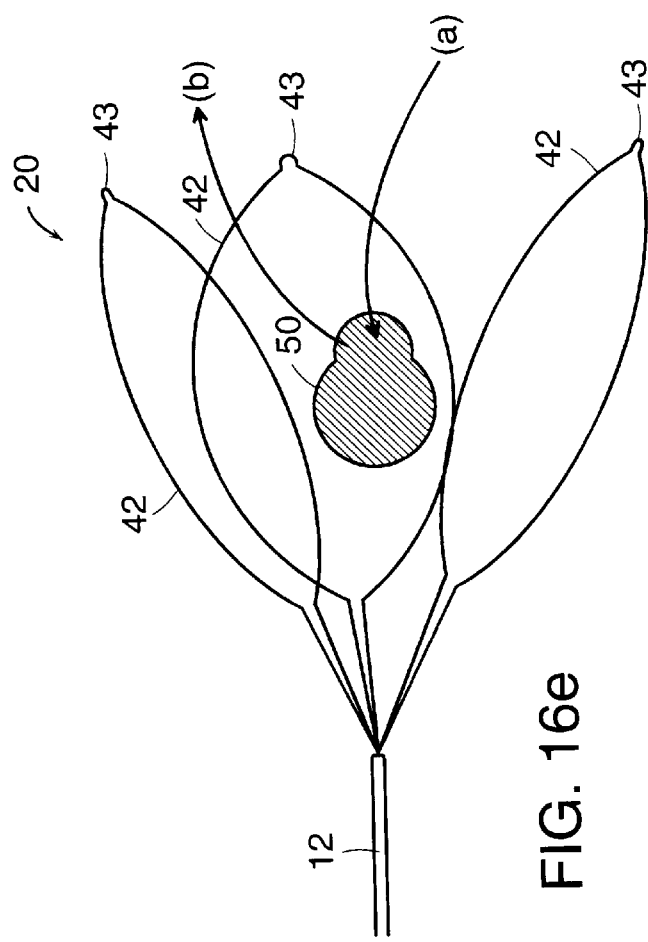
FIG. 16e is a side view of a loop retrieval assembly in the third position with a stone.

Referring to FIGS. 16*a*–16*c*, in another aspect of the invention, the medical retrieval instrument, including the elongated, expandable end-encapsulation loop retrieval assembly described immediately above, can be used in a method for retrieving material from within a body. Initially, an operator advances the medical retrieval instrument 10 into the body, for example the urinary tract 60, while the retrieval assembly 20 is entirely enclosed within sheath 12, i.e., in the first position shown in FIG. 16*a*. The retrieval assembly 20 and sheath 12 may be inserted, for example, in the kidney via a nephroscope or inserted in the ureter via a ureterscope. When the distal end 15 of the sheath 12 approaches material such as a stone or stones 50, the operator retracts the sheath 12 axially with respect to the retrieval assembly 20 unsheathing the distal basket portion 24 from the distal end 15 of the sheath 12. The retrieval assembly 20 expands to the second (open) position as shown in FIG. 16*b*. In a method for retrieving material from the body, the retrieval assembly 20 expands to the third position as shown in FIGS. 16*e* and 16*f*.

The retrieval assembly 20 is advanced further into the body tract 60 until the stone or stones 50 is captured by end-encapsulation or side-encapsulation. End-encapsulation occurs when the stone 50 passes between the parted unattached ends 43 of the open retrieval assembly 20 as illustrated by arrows (a) in FIGS. 16*e* and 16*f*. Side-encapsulation occurs when the stone 50 passes between loops or through loops as shown from the side in FIG. 16*c* and from the end in FIG. 16*d*. After the stone 50 is positioned within the lumen of the retrieval assembly 20, the retrieval assembly 20 may be returned towards a closed position. The unattached ends 43 of the retrieval assembly loops 42 are substantially juxtaposed entrapping the stone 50 within the retrieval assembly 20. It is not essential to the operation of the retrieval assembly 20 that the unattached ends 43 of the retrieval assembly loops 42 actually meet. For particularly large stones, for example, the diameter of the stone 50 will prevent juxtaposition of the unattached ends of the retrieval assembly 20. However, the essential feature of successful encapsulation for stone removal is sufficient contact between the inner surface of the retrieval assembly loops 42 with the stone 50 surface so that the stone 50 does not inadvertently slip out of the retrieval assembly 20.

Alternatively, the stone 50 may be released from the retrieval assembly 20 by advancing the retrieval assembly 20 from the end 15 of the sheath 12 to expose the proximal retrieval assembly portion 22. The gap between the unattached ends 43 of the retrieval assembly loops 42 at the distal end of the retrieval assembly, and the gaps between the loops 42 are increased thereby enhancing the ease by which the stone 50 may be released between the parted, unattached loop ends 43 or between the loops 42. As shown by arrows (b) in FIG. 16*e*, a stone 50 may pass from the lumen of the retrieval loop assembly 20 between the parted unattached loop ends 43 when the retrieval assembly is in position 3. Alternatively, a stone 50 may pass from the lumen of the retrieval loop assembly 20 through the loops (arrow (b)) or between the loops (arrow (c)) when the retrieval assembly is in position 3 as illustrated in FIG. 16*f*. The retrieval assembly 20 can be returned to the first position by withdrawing the retrieval assembly 20 completely into the sheath 12 and removed from the body or repositioned to encapsulate other stones.

Figure 17A:
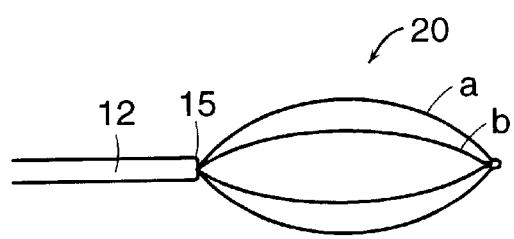
FIG. 17a is a side view of a two-loop embodiment of the retrieval assembly.
Figure 17B:
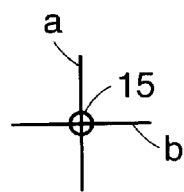
Figure 17C:
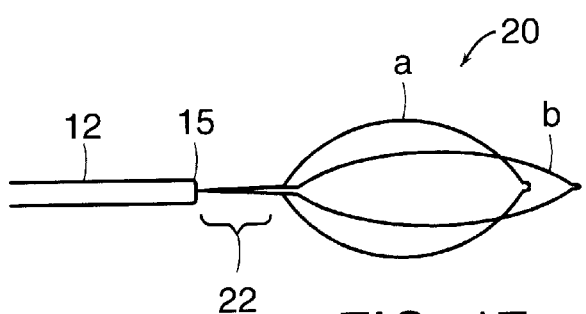
FIG. 17c is a side view of a two-loop embodiment of the retrieval assembly.
Figure 17D:
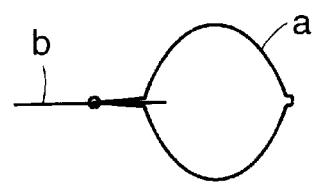
FIG. 17d is an end-view of the embodiment illustrated in FIG. 17c.
Figure 17E:
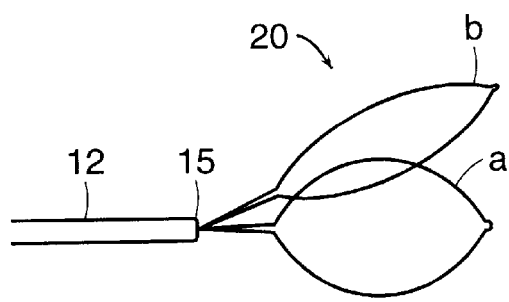
FIG. 17e is a side view of a two-loop embodiment of the retrieval assembly.
Figure 17F:
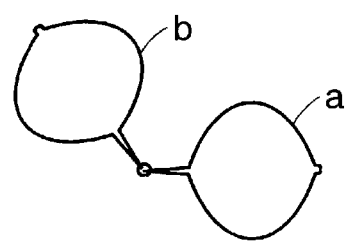
FIG. 17f is an end-view of the embodiment illustrated in FIG. 17e.

The medical instrument having the loop retrieval assembly described above may have a different number of loops than three loops, such as two, four, five or more loops. In FIG. 17*a*, a side view of a two-loop basket in position 2 is shown. In FIG. 17*b*, an end-view of the basket shown in FIG. 17*a* is illustrated. A two-loop retrieval assembly in position 3 is illustrated from the side in FIGS. 17*c* and 17*e* and from the end in FIGS. 17*d* and 17*f*, respectively.

It will be apparent to those skilled in the art that various modifications and variations can be made to the structure and methodology of the present invention without departing from the scope or spirit of the invention. In view of the foregoing, it is intended that the present invention cover modifications and variations of this invention provided they fall within the scope of the following claims and their equivalents.

What is claimed is:

1. A medical instrument comprising:

a proximal handle;

a sheath including a proximal portion and a distal end, the proximal portion of the sheath coupled to the handle; and a retrieval assembly comprising
- a plurality of legs, at least one of said legs comprising
  - a bulbous proximal portion formed in a proximal portion of said at least one of said plurality of legs, and comprising a proximal end, a distal end, and an intermediate section, said plurality of legs being closer together at said distal end of said bulbous proximal portion than in said intermediate section of said bulbous proximal portion, and
  - a bulbous distal portion formed in a distal portion of said at least one of said plurality of legs, and comprising a proximal end, a distal end, and an intermediate section, said plurality of legs being closer together at said proximal end of said bulbous distal portion than in said intermediate section of said bulbous distal portion,
    - wherein said bulbous distal portion formed in said distal portion of said at least one of said plurality of legs of said retrieval assembly captures material in a body when said bulbous distal portion of said retrieval assembly extends from said distal end of said sheath and said bulbous proximal portion of said retrieval assembly is collapsed within said sheath, said retrieval assembly expanding to release captured material when said distal and proximal portions of said retrieval assembly extend from said distal end of said sheath.

2. The medical instrument of claim 1 wherein said retrieval assembly comprises a basket.

3. The medical instrument of claim 2 further comprising at least three sets of paired, helical basket legs.

4. The medical instrument of claim 2 further comprising an atraumatic basket.

5. The medical instrument of claim 2 wherein said basket is preformed basket legs.

6. The medical instrument of claim 1 wherein said sheath is
- axially moveable over said retrieval assembly, whereby said retrieval assembly transitions between at least first, second, and third positions when said sheath is axially moved.

7. The medical instrument of claim 1 further comprising:
- an elongated guide member extending within a lumen of said sheath and operably attached to said retrieval assembly, whereby said retrieval assembly moves between at least first, second, and third positions when said elongated guide member is axially moved within said sheath.

8. The medical instrument of claim 1 further comprising at least three retrieval assembly portions.

9. The medical instrument of claim 1 wherein said handle is removable.

10. The medical instrument of claim 1 wherein said sheath further comprises:
- at least two compressible slits, whereby compression of said slits causes said sheath to retract from said retrieval assembly.

11. A method for retrieving biological materials in a body, comprising the steps of:
- inserting a medical instrument into the body, the instrument comprising a handle, a sheath with a lumen, a proximal portion and a distal end, the proximal portion of the sheath coupled to the handle, and
- a retrieval assembly comprising
  - a plurality of legs,
  - a bulbous proximal portion wherein said legs of the bulbous proximal portion comprise a proximal end, a distal end, and an intermediate section, the distal ends of the legs of the bulbous proximal portion being closer together than the intermediate section of the legs of the bulbous proximal portion, and,
  - a bulbous distal portion wherein the legs of the bulbous distal portion comprise a proximal end, a distal end, and an intermediate section, the proximal ends of the legs of the bulbous distal portion being closer together than the intermediate section of the legs of the bulbous distal portion,
    - wherein the bulbous distal portion of said retrieval assembly captures material in a body when the bulbous distal portion extends from the distal end of the sheath, the retrieval assembly expanding when the distal and proximal portions of the retrieval assembly extend beyond the distal end of the sheath;
    - extending the bulbous distal portion of the retrieval assembly beyond the distal end of the sheath;
    - capturing material within the retrieval assembly;
    - extending the bulbous proximal portion of the retrieval assembly beyond the distal end of the sheath; and,
    - releasing captured material from the retrieval assembly.

12. The method of claim 11 further comprising the step of:
- extending the proximal portion of the retrieval assembly beyond the distal end of the sheath and capturing material within the retrieval assembly.

\* \* \* \* \*